United States Patent
Shepherd

(10) Patent No.: US 6,492,419 B1
(45) Date of Patent: Dec. 10, 2002

(54) AQUEOUS INSECTICIDAL POUR-ON FORMULATION

(75) Inventor: Stanley Shepherd, Sydney (AU)

(73) Assignee: Schering-Plough Animal Health Corp., Union, NJ (US)

(*) Notice: Subject to any disclaimer, the term of this patent is extended or adjusted under 35 U.S.C. 154(b) by 0 days.

(21) Appl. No.: 09/581,387

(22) PCT Filed: Dec. 18, 1998

(86) PCT No.: PCT/AU98/01046

§ 371 (c)(1),
(2), (4) Date: Aug. 15, 2000

(87) PCT Pub. No.: WO99/32088

PCT Pub. Date: Jul. 1, 1999

(30) Foreign Application Priority Data

Dec. 19, 1997 (AU) .............................................. PP1054

(51) Int. Cl.⁷ ........................ A01N 37/06; A01N 47/28; A61K 31/22; A61K 31/17; A61K 31/44

(52) U.S. Cl. ........................ 514/549; 514/596; 514/598; 514/345

(58) Field of Search ................................ 514/383, 596, 514/598, 549, 345

(56) References Cited

U.S. PATENT DOCUMENTS 5,849,320 A * 12/1998 Turnblad et al. ............ 424/410

FOREIGN PATENT DOCUMENTS

| JP | 07247207 | * | 9/1995 |
| KR | 9501845 | * | 3/1995 |

\* cited by examiner

*Primary Examiner*—Alton Pryor
(74) *Attorney, Agent, or Firm*—Palaiyur S. Kalyanaraman; Robert L. Bernstein

(57) ABSTRACT

A topically acceptable aqueous pour-on formulation adapted for localized external application to an animal, which format includes an effective amount of a water insoluble insect growth regulator (IGR), a suspending agent, a surfactant or mixture of surfactants, and an aqueous carrier.

14 Claims, No Drawings

AQUEOUS INSECTICIDAL POUR-ON FORMULATION

This application is a 371 of PCT/AU98/01,046 filed Feb. 18, 1998.

FIELD OF THE INVENTION

The present invention relates to an aqueous pour-on formulation of water insoluble insect growth regulator (IGR), and a method of treating animals using this formulation.

BACKGROUND ART

Traditionally, animals have generally been treated for the control of parasites, by either dipping the whole animal in a bath containing a parasiticidally effective agent or by spraying the entire body surface of the animal with such an agent. More recently, it has been found that a number of parasiticidally effective substances may be applied by localised application (so-called "pour-on" application). Although the parasiticidally effective substance is supplied by localised application, the active agent migrates so as to protect the whole external surface of the animal. By "localised application" it is meant that the active ingredient is only applied to a minor portion of the outer surface of the animal, generally as a line or spot on the animal's back.

Prior Art Formulations (a) Non Aqueous Pour-On Formulations

Various pour-on formulations are described in Australian patent nos. 560078, 563723, and 546672. In most pour-on formulations, and in all current water insoluble IGR pour-on formulations known to the inventors, the active agent is dissolved in a non-aqueous solvent system to produce a suitable pour-on formulation.

It has become apparent that non-aqueous pour-on formulations also possess a number of disadvantages. In particular, the formulation may pose handling problems caused by the flammability or toxicity of the solvents, and lead to high tissue residue levels in animals treated with the formulations.

Formulations based on water immiscible solvents would either run off wet animals or be washed off by rainfall which occurred after treatment.

On contact with water, the active rapidly precipitates out of non-aqueous formulations which are based on water miscible solvents. If this formulation is applied to a wet animal, or if the animal is exposed to rain before the treatment has dried on the animal, the active precipitates out of solution and is deposited along the back of the animal, the solvents also being washed away by the rain. This hinders or prevents the spread of the active ingredient around the entire animal. This phenomenon is particularly important to those areas on the underside of the animal. This reduces the effectiveness of solvent only based formulations under these conditions.

(b) Aqueous Dip Formulations

An aqueous dip formulation of IGR is also known.

However, such a dip formulation would not be suitable as a pour-on formulation in either the undiluted or diluted state for the following reasons.

Undiluted Dip Formulation

This would not be satisfactory because:

(i) In order to deliver the same amount of active per animal, the dose volume would be too small. That is, 2 mL would be applied to the majority of animals, which would be a major issue for accurate dosing by farmers. A very small dose volume would be too localised to allow spreading to all parts of the animal as described above.

(ii) Due to the high levels of surfactants in an undiluted dip formulation, the presence of water, particularly high rainfall, would tend to wash the active off the animal.

Diluted Dip Formulation

This situation would arise where the above-mentioned dip formulation is diluted to achieve what would be considered a satisfactory concentration of active. However, this would not be satisfactory for the following reasons:

(i) If the dip formulation were diluted in a backpack or drum, the active would almost immediately commence to settle out of the formulation due to dilution of the suspending agent. This would create under/over dosing as described above.

(ii) Because the sedimented active would no longer be associated with the spreading/wetting agents, it would essentially be deposited along the line of application and have no means to disperse.

With regard to the possibility of aqueous pour-on formulations, and based on non-aqueous pour-on formulations, it would be expected by those skilled in this art that aqueous pour-on formulations containing water insoluble IGRs would not be effective because of problems with spreading and physical stability as follows.

Spreading

It has generally been believed that a non-aqueous solvent is required to both dissolve the water insoluble IGR and help disperse the active so that it reaches all parasites on the animal. Without such spreading, the active would not reach all of the parasites, and would therefore be ineffective. Such spreading, in particular with sheep, also involves the movement of the active into the greasy layer of the wool. This is facilitated by the solvents which "push" the active into the layer while at the same time providing the physical spreading described above.

Physical Stability

Because of the insolubility of the IGR in water, it is necessary to "suspend" the active in the formulation so that it does not settle on standing. If such settling occurs to a significant degree, then it is difficult to redisperse it to achieve an accurate dose rate for application to the animal. Thus, there is in effect a caking of the active at the bottom of the container. This is a major reason why many aqueous suspensions have problems. The result is that an animal treated with product from the upper part of the container is underdosed, while an animal treated with the product from the lower part of the container is overdosed. This may have fatal consequences.

Aqueous formulations of water insoluble IGRs are more accurately described as suspensions. It would be expected that when such formulations are applied to animals as pour-ons, the suspended active would remain at the site of application, thereby exacerbating the spreading problems described above. Furthermore, it has been shown that when other water insoluble actives are applied to animals such as sheep in an aqueous pour-on formulation, the majority of the active grows out with the wool staple, effectively being carried away from the skin surface where it is needed to control the parasites.

DISCLOSURE OF THE INVENTION

It has now been surprisingly found that an aqueous based pour-on formulation containing a water insoluble insect growth regulator(IGR) and a blend of surfactant and wetting agents is efficacious in controlling sheep lice. The formulation has the advantage over traditional non-aqueous solvent based formulations because it is rainfast and leads to very low pesticide tissue residue levels in the animals after application.

A surprising demonstration of the efficacy of this pour-on formulation is that at concentrations of 12.5 and 25.0 g/L diflubenzuron, when applied as a 20 ml dose along the backline of sheep, 100% lice kills were reported within 20 weeks. The majority of lice (95%) were killed within 10 weeks of application with the rest being killed over the remainder of the 20 week period.

It has also surprisingly been found that adding the formulations of this invention to an already wet animal does not affect the efficacy of the formulation. Likewise, if it rains shortly after the formulations of this invention are applied, the speed of efficiency of the active is increased compared to situations where no rainfall occurs after treatment. In both instances, it is believed that the surfactants promote the spread of the active over the surface of the animal.

Thus, in a first aspect, the present invention provides a topically acceptable aqueous pour-on formulation adapted for localised external application to an animal, which formulation includes an effective amount of a water insoluble insect growth regulator (IGR), a suspending agent, a surfactant or mixture of surfactants, and an aqueous carrier.

Because of the insolubility of IGR in water, it is necessary to suspend the active in the formulation so it does not settle on standing. Accordingly, it is necessary to include in the formulation a sufficient amount of a suspending agent.

In a second aspect, the present invention provides a method for controlling external parasites on an animal which method includes externally applying to an animal an effective amount of a aqueous pour-on formulation adapted for localised external application to an animal, which formulation includes an effective amount of a water insoluble IGR, a suspending agent, a surfactant or mixture of surfactants, and an aqueous carrier.

Any water insoluble IGR could be used in the formulation according to the present invention. Suitable IGRs include diflubenzuron, triflumuron, fluazuron, and methoprene. A particularly preferred IGR is diflubenzuron. For the formulation to be effective, the IGR must be suspended in the aqueous carrier.

Suitable suspending agents include xanthan gum, colloidal silica, bentonite, polyvinyl pyrrolidone, cellulose derivatives and alginates. The particularly preferred suspending agent is xanthan gum.

Any anionic or nonionic surfactant could be used in this formulation. A preferred anionic surfactant is alkylated naphthalene sulphonate, formaldehyde polymer, sodium salt. An effective amount of surfactant must be incorporated into the formulation to provide sufficient dispersant activity when applied to the animal. Preferred non-ionic surfactants are alkyl polysaccharides; alkyl phenol ethoxylates. A preferred alkyl phenol ethoxylate is nonyl phenol ethoxylate.

Other ingredients may be suitably included, for example, wetting agents, thickeners, humectants, preservatives, buffers, anti-foaming agents, diluents, excipients, adjuvants, and/or carriers. Actives which have an immediate effect (ie "knock down"); dyes (scourable, water soluble); antioxidants or UV stabilizers (eg oxybenzone); and thixatropic agents may also be added. A preferred humectant is polyethylene glycol.

Thus, in a third aspect, the present invention provides a method for formulating a topically acceptable aqueous pour-on formulation adapted for localised external application to an animal, which method comprises forming a first component by mixing a humectant and non-ionic surfactant until homogenous; adding water and mixing until homogenous; adding buffer and anionic surfactant; adding insect growth regulator (IGR); forming a second component by mixing humectant and thickener; and combining said first and second components.

Suitably, the first and second components are diluted to a desired and final volume.

In addition, suitably, the IGR is milled to form a particle size of between about 2 to about 5 $\mu$m.

| Suitable ranges for the ingredients are as follows: | |
|---|---|
| a) Active | 5–50 g/L |
| b) Surfactants (non-ionic) | 10–100 g/L |
| c) Surfactants (anionic) | 1–20 g/L |
| d) Wetting Agent | 1–20 g/L |
| e) Thickener | 3–10 g/L |

The "normal" ratio of the above would be a) :b) :c) :d) :e)=5:6:1:1:1. A more general description of the ratio would be active:surfactants/wetting agents/thickeners=1:2. These ratios would not be expected to vary significantly with type of active or surfactants. The most effective ratio is that of the most preferred formulation which has been "balanced" to optimise all of the above. The optimum pH for this formulation is in the range pH 5–9.

A particularly preferred formulation using the ranges of concentrations above would include diflubenzuron as the active; nonyl phenol ethoxylate, alkylated naphthalene sulfonate, formaldehyde polymer, sodium salt, as the mixture of surfactants; sodium lauryl sulfate as a wetting agent and Xanthan gum as a thickener or suspending agent.

Suitably, pour-on formulations include a colouring agent to enable the user to visually monitor the application of the formulation to the animal. The nature of the coloring agent is unimportant and a wide variety of suitable dyes and pigments will be known to the skilled person.

Suitably, the ingredients are formulated as follows: (a) half of the propylene glycol and non-ionic surfactant mixed in a mixing vessel until homogeneous. Water is then added and mixed until homogeneous. This is followed by buffer and anionic surfactant. Typically, anti-foam is then added and the mixture stirred. (b) The active ingredient is then added and mixed until homogeneous. (c) The second half of the propylene glycol is mixed with the Xanthan gum and then added and again, the mixture stirred well until thorough mixing has occurred. The final volume is then adjusted with water if necessary.

The pour-on formulation may be formulated for application by a spray technique, for example, as an aerosol using a liquid or gas as propellent.

Depending on the efficacy of the particular active agent used, the formulation will generally contain from about 5 to about 50 g/L of the active agent.

The external parasites which may be treated in accordance with this invention include ticks, fleas, flies (for example, sheep blow fly, buffalo fly, nuisance fly), lice (for example, cattle and sheep lice) and mites (for example, sheep mites). The insects and parasites mentioned are indicative only, and numerous other insects and parasites can be treated by the method of the present invention. Suitably, the compositions and method of this invention may be used to treat the sheep body louse which is classified as follows: Order—

Phthiraptera, Sub Order—Mallophaga, Family—Trichodectidae, Genus—Damalinia (Bovicola, Tricholdectes), Species—*Bovicola ovis* (Schrank).

The animal is preferably a mammal, and may be selected from sheep, cattle, deer, goats, pigs, dogs, and cats. The animal may also be a bird.

BEST AND OTHER MODES FOR CARRYING OUT THE INVENTION

Preferred embodiments will now be described by way of non-limiting examples.

EXAMPLE 1

TABLE 1

Diflubenzuron Sheep Lice Pour-on (25 g/L)

| Component | Use | (g/L) |
| --- | --- | --- |
| Diflubenzuron | Active Ingredient | 25.00 |
| Nonyl phenyl ethoxylate (eg. Teric GN15) | Non ionic | 30.00 |
| Alkylated naphthalene sulfonate, formaldehyde polymer, Sodium salt (eg. Morwet D425) | Anionic surfactant | 3.00 |
| Sodium lauryl sulphate BP (eg. Empicol LZVD) | Wetting agent | 5.00 |
| Xanthan Gum USP (eg. Keltrol F) | Thickener | 5.10 |
| Propylene Glycol USP | Humectant | 60.00 |
| 1,2-Benzisothiazoline-3-one (20% w/w) in aqueous dipropylene gycol Solution (eg. Proxel GXL) | Preservative | 1.00 |
| Simethicone USP (eg. Antifoam A) | Antifoam | 1.00 |
| Citric Acid (Anhydrous BP) | Buffer | 1.01 or qs |
| Disodium hydrogen phosphate-Anhydrous Food Grade | Buffer | 13.30 or qs |
| Deionised Water | Diluent | qs to 1 L |

EXAMPLE 2

Details of Trial

Target Pest

Order—Phthiraptera, Sub Order—Mallophaga, Family—Trichodectidae, Genus—Damalinia (Bovicola, Trichodectes), Species—*Bovicola ovis* (Schrank) and Common name—Sheep body louse.

Test Animals

The sheep used in this study were a uniform line of Merino wethers heavily infected with lice.

The method requires examination of twenty partings each 10 cm long, along two contours on the left and right sides covering the wool growing regions of the animal. At each of the 40 recorded sites all live adult lice are counted. Site counts are summed to give a total count for the animal.

Assessing lice populations in this manner also allows the production of a map, showing how the lice are distributed over the body of the tracer sheep.

TABLE 2

Treatment details

| Treatment | Active (mg) per sheep | Conc (g/L) | Sheep | Dose (mL) |
| --- | --- | --- | --- | --- |
| Diflubenzuron | 500 | 25.0 | 5 | 20 |
| Diflubenzuron | 250 | 12.5 | 5 | 20 |

Test Treatments

Within 24 hours of shearing, treatments were applied as a single stripe along the backline of the sheep. The dose rate applied was based on 20 mL of treatment per animal which is based on all test animals being in the 30.1–55 kg weight range.

The delivery apparatus for each formulation was a commercial applicator, set to deliver 1×20 mL doses to the sheep backline. The gun was calibrated using a volumetric cylinder and checked twice before and once after treatment.

To avoid the possibility of rain complicating the post treatment situation the sheep were kept in pens for a minimum of 48 hours. Then on the morning of the 25 th day of the trial, they were placed into their paddocks.

Lice assessments were made on all sheep 2, 5, 10 and 20 weeks after treatment.

EXAMPLE 3

Effect of Diflubenzuron Formulations on Concentrations of Sheep Lice [Group Arithmetic Lice Counts (Standard Deviations)]

TABLE 3

Mean Lice Counts

| Diflubenzuron | Weeks after treatment | | | | | |
| --- | --- | --- | --- | --- | --- | --- |
| (g/L) | 0 | 2 | 5 | 10 | 15 | 20 |
| 25.0 | 120.6 (74.2) | 17.2 (9.0) | 4.4 (7.7) | 1.4 (2.6) | 1.0 (1.4) | 0.0 (0.0) |
| 12.5 | 161.8 (124.7) | 6.8 (2.9) | 1.8 (2.50) | 0.4 (0.9) | 0.0 (0.0) | 0.0 (0.0) |

TABLE 4

Field Efficacy (Control of sheep lice) Diflubenzuron Concentration is 25 g/L

| Trial No | Location | Animal Used | Pre treatment mean lice count | % Lice reduction after: | | |
| --- | --- | --- | --- | --- | --- | --- |
| | | | | 6 weeks | 12 weeks | 20 weeks |
| 1 | Uraila, N.S.W. | 1309 fine wool merinos | 156 | 98.1 | 98.7 | 100 |
| 2 | Guyra, N.S.W. | 2000 super fine wool | 41 | 100 | 100 | 100 |
| 3 | Crookwell, N.S.W. | 680 medium fine wool merinos | 242 | 91.3 | 99.6 | 100 |
| 4 | Lucindale, N.S.W | 1094 strong wool merinos | 35 | 99.8 | 100 | 100 |
| 5 | Coonalpyn, S.A. | 1101 strong wool merinos | 142 | 99.6 | 100 | 100 |
| 6 | Lismore, Vic | 812 super fine merinos | 51 | 99.5 | 100 | 100 |

EXAMPLE 4

Efficacy Trial

Effect of diflubenzuron in 12.5 and 25.0 g/L pour-on formulations (corrected lice counts) [Results of Table 3 converted to % lice reduction]

TABLE 5

| Diflubenzuron | % Lice reduction after: | | | | |
|---|---|---|---|---|---|
| (g/L) | 2 weeks | 5 weeks | 10 weeks | 15 weeks | 20 weeks |
| 25.0 | 69.6 | 83.4 | 94.8 | 96.4 | 100.0 |
| 12.5 | 91.0 | 94.9 | 98.9 | 100.0 | 100.0 |

EXAMPLE 5

Results of Wetting Trial

TABLE 6

Group mean lice counts

| Group No | Treatment | Wetting | Days Post Treatment | | | | |
|---|---|---|---|---|---|---|---|
| | | | 0 | 22 | 44 | 84 | 142 |
| 1 | 25 g/L diflubenzuron | No wetting | 92.0 | 2.5 | 0.5 | 0.3 | 0.2 |
| 2 | 25 g/L diflubenzuron | 25 mm rain before treatment | 105.5 | 5.8 | 0.3 | 0.2 | 0.0 |
| 3 | 25 g/L diflubenzuron | 25 mm rain after treatment | 110.0 | 0.7 | 1.2 | 0.3 | 0.0 |
| 4 | Untreated | 25 mm rain before treatment | 92.7 | 13.5 | 10.5 | 2.2 | 17.0 |
| 5 | Untreated | No wetting | 106.3 | 15.7 | 7.0 | 2.0 | 17.5 |

TABLE 7

Effect of rain on diflubenzuron pour-on (percent reductions)

| Group No | Treatment | Wetting | Days Post Treatment | | | |
|---|---|---|---|---|---|---|
| | | | 22 | 44 | 84 | 142 |
| 1 | 25 g/L diflubenzuron | No wetting | 81.6 | 86.8 | 82.7 | 98.7 |
| 2 | 25 g/L diflubenzuron | 25 mm rain before treatment | 62.8 | 95.7 | 89.9 | 100.0 |
| 3 | 25 g/L diflubenzuron | 25 mm rain after treatment | 95.7 | 83.6 | 85.6 | 100.0 |
| 4 | Untreated | No wetting | 1.4 | −72.0 | −26.1 | −11.4 |

Note that these reductions have been calculated using the mean lice counts of Group 5, that is, the sheep kept dry. The following formula was used to calculate percent lice reductions.

% reduction=[1−(Untreated PT/Treated PT×Treated Time T/Untreated Time T)]×100, where PT is average lice number, and T is the average lice number at time post treatment.

EXAMPLE 6

Pen Efficacy Trial (Control of Cattle Lice)

Efficacy of 25 g/L diflubenzuron pour-on against cattle lice.

TABLE 8

| Group No | Dose Rate mg/kg | Pre treatment mean lice counts | % Lice reduction after: | | | | | |
|---|---|---|---|---|---|---|---|---|
| | | | 14 days | 28 days | 42 days | 60 days | 72 days | 84 days |
| 1 | 5 | 99 | 57.7 | 52.5 | 94.8 | 92.2 | 95.7 | 87.9 |
| 2 | 10 | 89 | 68.7 | 62.9 | 96.2 | 99.3 | 98.1 | 100 |
| 3 | 15 | 97 | 81.9 | 62.7 | 94.6 | 95.1 | 99.0 | 100 |

EXAMPLE 7

Field Efficacy (Prevention of Strike by Sheep Blowfly)

Fourteen field efficacy trials were carried out under a range of climatic conditions throughout the eastern states of Australia. The data generated showed that the 25 g/L diflubenzuron formulation gave a high level of protection against body and crutch strike. Less than 0.1% of the 2316 sheep treated suffered body strike and 0.35% crutch strike. Fly pressure was measured using 2 flytraps within each paddock housing the treated sheep.

EXAMPLE 8

Pen Efficacy Trials (Larval Implant Studies to Demonstrate Efficacy Against Strike by Sheep Blowfly, Lucilia Cuprina)

Pen studies have demonstrated that the aqueous product, when applied as a spray-on along the backline of long wooled sheep, is efficacious against the larval stages of the sheep blowfly, Lucilia cuprina.

EXAMPLE 9

Tissue Residues

Tissue residue studies were carried out following application of the aqueous pour-on to both sheep and cattle (Reference is made to page 1, lines 34 and 35 where it is mentioned that treatment with non aqueous pour-on formulations can lead to high tissue residues in animals treated with these formulations.)

TABLE 9

Sheep: Diflubenzuron residues after treating at a dose rate of 20 mg/kg

| Days post treatment | Level of diflubenzuron residues in tissues (mg/kg) | | | | |
|---|---|---|---|---|---|
| | Muscle | Liver | Kidney | peri-renal fat | Inguinal fat |
| 1 | <LOQ | <LOQ | <LOQ | 0.03 max | 0.02 max |
| 3 | <LOQ | <LOQ | <LOQ | 0.02 max | 0.04 max |
| 7 | <LOQ | <LOQ | <LOQ | 0.02 max | 0.03 max |
| 14 | <LOQ | <LOQ | <LOQ | <LOQ | 0.02 max |
| 21 | <LOQ | <LOQ | <LOQ | <LOQ | 0.05 max |
| 42 | <LOQ | <LOQ | <LOQ | <LOQ | <LOQ |

Note: Limit of quantitation (LOQ) = 0.02 mg/kg

TABLE 10

Cattle: Diflubenzuron residues after treating at a dose rate of 15 mg/kg

| Days post treatment | Level of diflubenzuron residues in fat tissues (mg/kg) | |
| --- | --- | --- |
| | Peri-renal fat | Inguinal fat |
| 1 | 0.17 | <LOQ |
| 3 | 0.09 | <LOQ |
| 7 | <LOQ | <LOQ |
| 14 | <LOQ | <LOQ |

Note:
1. Limit of quantitation (LOQ) = 0.02 mg/kg
2. Muscle, liver and kidney tissues have not been tested as the diflubenzuron will preferentially go into the fat tissues.

EXAMPLE 10

Comparative Stability of Formulations Containing Nominally 25 g/L Diflubenzuron and 25g/L Triflumuron.

TABLE 11

Stability of aqueous triflumuron pour-on after 6 weeks accelerated testing

| Storage Temp. | Appearance | pH | Viscosity Cps | Assay g/L |
| --- | --- | --- | --- | --- |
| 4° C. | Purple suspension | 7.59 | 922 | 24.0 |
| 30° C. | Purple suspension | 7.53 | 800 | 24.2 |
| 40° C. | Purple suspension | 7.48 | 772 | 23.6 |
| 50° C. | Purple suspension | 7.44 | 818 | 24.1 |

TABLE 12

Stability of aqueous diflubenzuron pour-on after 16 weeks accelerated testing

| Storage Temp | Appearance | pH | Viscosity Cps | Assay g/L |
| --- | --- | --- | --- | --- |
| 4° C. | Purple suspension | 7.56 | 835 | 25.1 |
| 30° | Purple suspension | 7.48 | 821 | 25.3 |
| 40° C. | Purple suspension | 7.48 | 855 | 26.0 |
| 50° C. | Purple suspension | 7.50 | 913 | 26.0 |

SUMMARY

Efficacy data shows that rainfall pre or post treatment does not affect the efficacy of the formulation i.e. the product will be rainfast.

Insect growth regulators act by preventing the formulation of chitin during the insects moulting phase. They prevent the development of immature lice present in the fleece at the time of application and those which hatch from eggs in the following weeks. Adult lice die out naturally over a few weeks (can take up to 14).

The surprisingly quick knockdown effect (95.7% reduction in lice) of the formulation after post treatment rainfall (22 days) is shown. Four out of six sheep in the group had no lice present. This demonstrates that the surfactants do help to spread the formulation when the product is applied in the wet.

The foregoing describes only some embodiments of the present invention and modifications obvious to those skilled in the art can be made thereto without departing from the scope of the invention.

INDUSTRIAL APPLICABILITY

It should be clear that the present invention will find wide applicability in the agricultural and veterinary science areas.

What is claimed is:

1. A topically acceptable aqueous pour-on formulation adapted for localized external application to an animal, which formulation consists essentially of an effective amount of water insoluble insect growth regulator (IGR), a suspending agent, an anionic surfactant, a non-ionic surfactant or mixtures thereof, and an aqueous carrier, wherein said IGR is selected from the group consisting of diflubenzuron, triflumuron, fluazurin and methoprene, said suspending agent is selected from the group consisting of xanthan gum, colloidal silica, bentonite, polyvinylpyrrolidone, cellulose and alginates, and said surfactant or surfactants are selected from the group consisting of alkylated naphthalene sulfonate, formaldehyde polymer sodium salt, alkyl polysachcharides, and alkyl phenol ethoxylates, and optionally wetting agents, thickeners, humectants, preservatives, buffers, anti-foaming agents, diluents, excipients, adjuvants, and/or carriers, dyes, and antioxidants.

2. The formulation according to claim 1 wherein the suspending agent is xanthan gum.

3. The formulation according to claim 1 wherein the humectant is polyethylene glycol.

4. The formulation according to claim 3 wherein the IGR is about 5–50 g/L; the anionic surfactant is about 1–20 g/L; the non-ionic surfactant is about 10–100 g/L; the wetting agent is about 1–20 g/L and the thickener is about 3–10 g/L.

5. A method for controlling external parasites which method includes externally applying to an animal an effective amount of an aqueous pour-on formulation adaped for localized external application to an animal, which formulation consists essentially of an effective amount of water insoluble insect growth regulator (IGR), a suspending agent, an anionic surfactant, a non-ionic surfactant or mixtures thereof, and an aqueous carrier, wherein said IGR is selected from the group consisting of diflubenzuron, triflumuron, fluazurin and methoprene, said suspending agent is selected from the group consisting of xanthan gum, colloidal silica, bentonite, polyvinylpyrrolidone, cellulose and alginates, and said surfactant or surfactants are selected from the group consisting of alkylated naphthalene sulfonate, formaldehyde polymer sodium salt, alkyl polysachcharides, and alkyl phenol ethoxylates, and optionally wetting agents, thickeners, humectants, preservatives, buffers, anti-foaming agents, diluents, excipients, adjuvants, and/or carriers, dyes, antioxidants, and a propellant.

6. The method according to claim 5 wherein the formulation is applied as a spray technique.

7. The method according to claim 5 wherein said propellant is a liquid or gas.

8. The method according to claim 5 wherein the IGR is from about 5 to about 50 g/L.

9. The method according to claim 5 wherein the parasites include ticks, fleas, flies, lice and mites.

10. The method according to claim 9 wherein the flies may be sheep blow fly, buffalo fly or nuisance fly; the lice may be cattle or sheep lice; and the mites are sheep mites.

11. A method for formulating a topically acceptable aqueous pour-on formulation according to claim 1, which method consists essentially of forming a first component by mixing said humectant and said non-ionic surfactant until homogenous; adding water and mixing until homogenous, adding said buffer and said anionic surfactant; adding said insect growth regulator (IGR); forming a second component by mixing said humectant and said thickener; and combining said first and said second components.

12. The method according to claim 11 wherein the combined first and second components are diluted to a desired final volume.

13. The method according to claim 11 wherein the IGR is milled to form a particle size of between about 2 to about 5 μm.

14. A topically acceptable aqueous pour-on formulation adapted for localized external application to an animal, which formulation comprises:
   a) an affective amount of diflubenzuron wherein said diflubenzuron is present in amount from 5–50 g/L;
   b) Xanthan gum wherein said Xanthan gum is present in amount from 3–10 g/L;
   c) a surfactant or mixture of surfactants selected from nonylphenolethoxylate; alkylated naphthalene sulfonate, formaldehyde polymer or sodium salt, wherein said surfactant or mixture of surfactants are present in amount from 10–100 g/L;
   d) sodium lauryl sulfate, wherein said sodium lauryl sulfate is present in amount from 1–20 g/L; and
   e) an aqueous carrier.

* * * * *